(12) United States Patent
Wang et al.

(10) Patent No.: US 7,892,489 B2
(45) Date of Patent: Feb. 22, 2011

(54) LIGHT SCATTERING DEVICE HAVING MULTI-LAYER MICRO STRUCTURE

(75) Inventors: Hong Wang, Cupertino, CA (US); Zhimin Liu, San Jose, CA (US)

(73) Assignee: OptoTrace Technologies, Inc., Mountain View, CA (US)

( * ) Notice: Subject to any disclaimer, the term of this patent is extended or adjusted under 35 U.S.C. 154(b) by 938 days.

(21) Appl. No.: 11/754,912

(22) Filed: May 29, 2007

(65) Prior Publication Data

US 2007/0229817 A1 Oct. 4, 2007

(51) Int. Cl.
*G01N 21/00* (2006.01)
*G01N 21/03* (2006.01)
*G01J 3/44* (2006.01)

(52) U.S. Cl. .................. 422/60; 436/165; 356/301
(58) Field of Classification Search .................. 422/60; 436/165; 356/301
See application file for complete search history.

(56) References Cited

U.S. PATENT DOCUMENTS

| 5,581,091 | A | 12/1996 | Moskovits |
| 6,231,744 | B1 | 5/2001 | Ying |
| 6,361,681 | B1 | 3/2002 | de Nora |
| 6,464,853 | B1 | 10/2002 | Iwasaki |
| 6,610,463 | B1 * | 8/2003 | Ohkura et al. ............. 430/322 |
| 2002/0182970 | A1 | 12/2002 | Liu |
| 2003/0175472 | A1 | 9/2003 | Den |
| 2006/0049742 | A1 * | 3/2006 | Lee et al. .................... 313/496 |

* cited by examiner

*Primary Examiner*—Lore Jarrett
(74) *Attorney, Agent, or Firm*—Xin Wen

(57) ABSTRACT

A micro structure includes a silicon substrate, an adhesion layer on the silicon substrate, a bias layer on the adhesion layer, and structure layers on the adhesion layer. The two or more structure layers comprise different material compositions and a plurality of holes through at least two of the structure layers. Widths of the plurality of holes are in the range of 0.5-500 nm.

45 Claims, 13 Drawing Sheets

SECTION A-A

LIGHT SCATTERING DEVICE HAVING MULTI-LAYER MICRO STRUCTURE

The present patent application is related to commonly assigned U.S. patent application Ser. No. 10/852,787 (U.S. Pat. No. 7,384,792), entitled "Method of fabricating nano-structured surface and configuration of surface enhanced light scattering probe", filed May 24, 2004, and U.S. patent application Ser. No. 11/562,409 (U.S. Pat. No. 7,460,224), entitled "Arrays of nano structures for surface-enhanced Raman scattering", filed Nov. 21, 2006. U.S. patent application Ser. No. 10/852,787 claims priority to provisional U.S. patent applications 60/473,283 and 60/473,287, both filed on May 27, 2003, and provisional application 60/520,222 filed on Nov. 17, 2003. U.S. patent application Ser. No. 11/562,409 claims priority to provisional U.S. patent application 60/751,472, filed Dec. 19, 2005. The content of the above patent applications are incorporated herein by reference.

BACKGROUND

The present application relates to Raman scattering devices including a sensing substrate having a micro structure.

A limitation for conventional Raman spectroscopy is the weak Raman scattering signals for trace chemical detection. Techniques for increasing Raman scattering signals include Surface-Enhanced Raman Spectroscopy (SERS) and Surface-Enhanced Resonance Raman Spectroscopy (SERRS). Molecules of a trace chemical can be adsorbed on micro structural surfaces. It was discovered that noble metals on the surfaces of the micro structures could enhance the Raman scattering signal.

There remains a need for a micro structure that can be fabricated by well-controlled manufacturing techniques. There is also a need for a Raman scattering device having non-contaminated micro structures allow Raman scattering measurement to be conducted in the field.

SUMMARY

In a general aspect, the present application relates to a micro structure including a silicon substrate; an adhesion layer on the silicon substrate; a bias layer on the adhesion layer; and two or more structure layers on the adhesion layer, wherein the two or more structure layers comprise different material compositions and a plurality of holes through at least two of the two or more of structure layers, wherein widths of the plurality of holes are in the range of 0.5-500 nm.

In another general aspect, the present application relates to a micro structure including a silicon substrate; an adhesion layer on the silicon substrate; a bias layer on the adhesion layer; and a plurality of columns on the bias layer, wherein at least one of the plurality of columns or holes comprises two or more structure layers having different material compositions and have widths in the range of in the range of 0.5-500 nm.

In another general aspect, the present application relates to a method for fabricating a micro structure. The method includes forming an adhesion layer on a substrate; forming a thermal bias layer on the adhesion layer; two or more structure layers on the adhesion layer, wherein the two or more structure layers comprise different material compositions; forming an upper layer on the two or more structure layers; producing recesses or protrusions on the upper layer; removing portions of the upper layer to produce a mask having a plurality of openings; and forming a plurality of holes in the two or more structure layers or a plurality of columns having the two or more structure layers by removing portions of the two or more structure layers through the openings in the mask, wherein widths of the plurality of holes or columns are in the range of in the range of 0.5-500 nm, such as 5-200 nm.

In another general aspect, the present application relates to a method for a micro structure. The method includes forming an adhesion layer on a substrate, forming a bias layer on the adhesion layer two or more structure layers having different material compositions on the adhesion layer; forming an upper layer on the two or more structure layers, wherein the upper layer comprises a metallic material; anodizing at least a portion of the upper layer to produce a mask having a plurality of openings; and forming a plurality of holes in the two or more structure layers or a plurality of columns having the two or more layers by removing portions of the two or more structure layers through the openings in the mask, wherein the widths of the plurality of holes or columns are in the range of in the range of 0.5-500 nm.

Implementations of the system may include one or more of the following. The two or more structure layers can include three structure layers arranged in a sequence of ABC or ABA, wherein each of the symbols "A", "B", and "C" represents a structure layer having a different material. The two or more structure layers can include four structure layers arranged in a sequence of ABAB, ABAC, ABCA, ABCB, and ABCD, wherein each of the symbols "A", "b", "C" and "D" represents a structure layer having a different material. The two or more structure layers can include a layer sequence of $(AB)_n$, in which n is an integer and the symbols "A" and represent structure layers of different materials. The two or more structure layers can include a material selected from the group consisting of Ag, Au, Cu, Pt, Al, Fe, Co, Ni, Ru, Rh, Pd, Ag doped with chlorine or chloride, and Au doped with chlorine or chloride. The two or more structure layers can include a material selected from the group consisting of $TiO_2$, $SiO_2$, $Al_2O_3$, $Si_3N_4$, $Ta_2O_5$, Zn oxide, Sn oxide, Sb oxide, Ag oxide, and Au oxide. The two or more structure layers can include a material selected from the group consisting of Ethylene Chlorotrifluorethylene (ECTFE), Poly(ethylene-co-butyl acrylate-co-carbon monoxide) (PEBA), Poly(allylamine hydrochloride) (PAH), Polystyrene sulfonate (PSS), Polytetrafluorethylene (PTFE), Polyvinyl alcohol (PVA), Polyvinyl chloride (PVC), Polyvinyldene fluoride (PVDF), and Polyvinylprorolidone (PVP). Te two or more structure layers can include a material selected from the group consisting of GaAs, ZnS, ZnO, CdS, $Er^3$ in $SiO_2$, InGaN, InGaN/GaN, AlGaAs, InAgAs, GaAs/GaAlAs, GaN, 4H SiC, AlN, GaN, AlGaN/GaN, InP, InAlAs/InGaAs, Cs, Rb, diamond, InAs, AlSb/InAs, AlGaAs/InGaAs, InAlAs, InGaP, SiGe, Al, C, and Si. The adhesion layer can include a metallic material. The adhesion layer can include a material selected from a group consisting of Ti, Ni, Co. The bias layer can include a material selected from a group consisting of Cr, Pt, Ru, a Ni—Cr alloy, NiCrN, a Pt—Rh alloy, a Cu—Au—Co alloy, an Ir—Rh alloy, and a W—Re alloy. One or more surfaces in the plurality of holes can adsorb molecules of a trace chemical for detection of the trace chemical using Raman scattering. The bias layer can receive a bias voltage to enhance adsorption of molecules on the one or more surfaces in the plurality of holes for Raman scattering sensing of trace chemicals. The molecules can be adsorbed front a liquid, sol gel, a gas, an aerosol, or a mixture of liquid, sol gel, gas, and aerosol. At least a portion of the plurality of holes can be distributed substantially in a periodic array in the two or more structure layers. The center-to-center spacing between the adjacent holes in the plurality of holes can be in the range of 0.5-1,000 nm. The center-to-center spacing between the adjacent holes in the plurality of holes can be in the range of 5-200 nm. The micro structure can further include an upper layer on the two or more structure layers, wherein the plurality of holes intrude through the upper layer. The upper layer can include aluminum of PMMA. A width of the plurality of holes can be in the range of 5-200 nm. Te adhesion layer and the bias layer can be formed by a single substantially uniform layer. Depths of the plurality of holes can be in the range of 0.5 nm and 1000 nm.

Embodiments may include one or more of the following advantages. The disclosed systems and methods may enhance the intensity of the scattered light for detecting trace chemicals. Different material compositions in the multiple layers in a multi-layer nano structure also allow different types of chemical molecules to be adsorbed to the surfaces of the nano structures, which can enable the detection of more than one type of trace chemicals.

These and other objects and advantages of the present application will become obvious to those of ordinary skill in the art after having read the following detailed description of the preferred embodiment which is illustrated in the various drawing figures.

DETAILED DESCRIPTION

Figure 1:
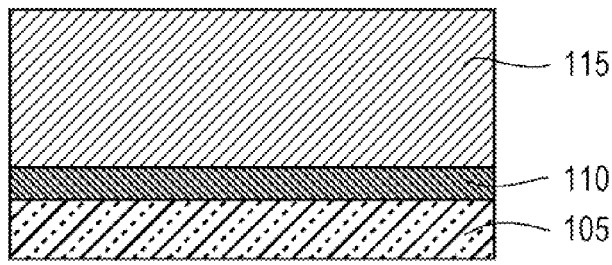
FIG. 1 is a cross sectional view of a three layer structure to start the process for fabricating a nano-structured surface.
Figure 2B:
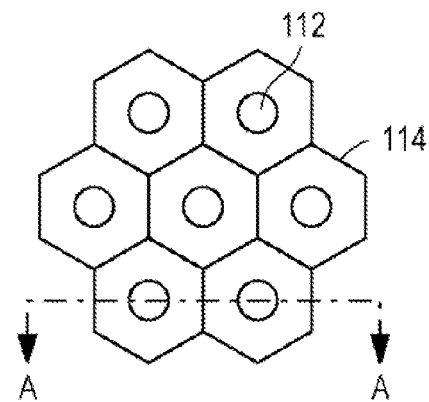
FIGS. 2A to 2C are respectively a cross sectional view of an assisting layer with holes formed by anodization process, a top view and a side cross sectional view along a horizontal line over the top view of FIG. 2B.
Figure 2A:
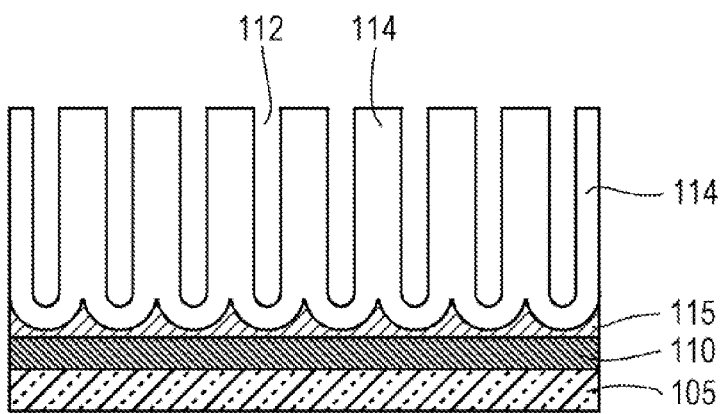
Figure 2C:
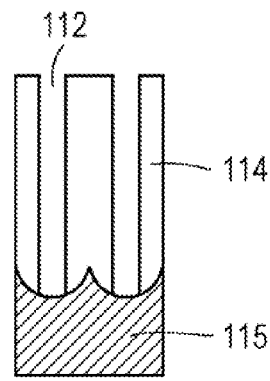
Figure 3:
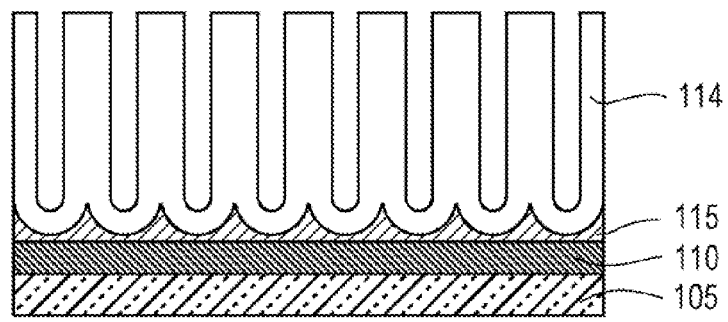
FIG. 3 shows a cross sectional view of the nano-structured surface after performing a chemical etch or CMP process.
Figure 4:
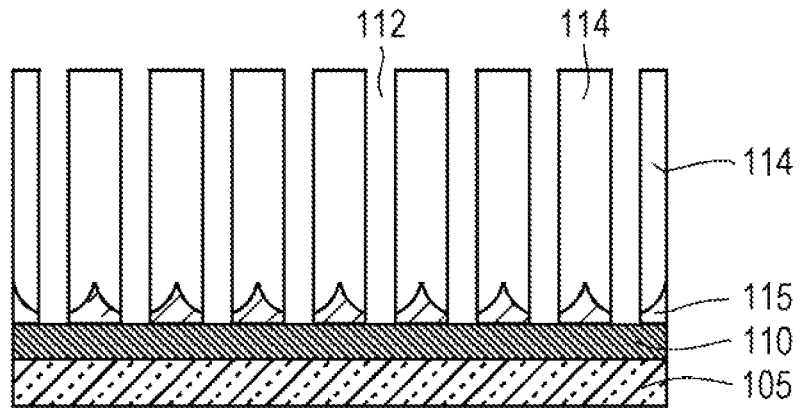
FIG. 4 shows a cross sectional view of the nano-structure surface after removing the barrier layer at the bottom of the holes and etching down to the conducting layer by chemical etching.

Referring to FIGS. 1 to 6 for a series of processing steps to fabricate a nano-structured noble metal surface of this application, FIG. 1 shows a two-layer structure with n-type (100) silicon wafer (3-8 Ω-cm) or oxidized (30-50 nm $SiO_2$) p-type (100) silicon wafers (5-10 mΩ-cm), an electrically and thermally conductive layer 110 deposited on a (100) silicon substrate 105. The thickness of the conductive layer 110, such as Ti and Ni, is optimized to provide i) best adhesion to a subsequently deposited noble metal film, such as Ag, or Au film, etc., ii) electrical conductive film to apply electrical bias to sensing surface in field application, iii) thermal conductive layer to apply lower temperature of sensing surface, iv) thermal heat sink film to conduct localized heat generated by excitation of a light source. The thickness of this metal film is usually controlled in the range of 50 Å-50,000 Å, or 100 Å-1,000 Å. Then an aluminum layer 115 with purity of 99.999% and thickness in the range of 2,000 Å-10.0 μm is deposited on top of the conductive layer 110. An anodization process is performed to produce a porous structure in a form of porous aluminum oxide layer 115 as that shown in FIG. 2A. FIG. 2B is a top view of the porous structure formed on the aluminum oxide layer 115 wherein the porous structure includes a plurality of pores 112 surrounded by pore wall 114 with the cross section view along a horizontal line A-A shown in FIG. 2C. Then wet oxide etch process is carried out in FIG. 3 to remove both top porous $Al_2O_3$ layer and barrier layer. A second anodization process is carried out to consume all Al metal so that the barrier layer and top porous $Al_2O_3$ layer are right above the conductive metal layer. In FIG. 4, an oxide etching is carried out to remove the barrier layer at the bottom of the pores and to widen the pore diameter. After the completion of the wet etch process, the pores 112 are extended downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) depends on applied anodization voltage (V), current density (i) and electrolyte, and the subsequent pore widening wet etch process; while the inter-pore distance (D) depends on applied anodization V, i and electrolyte. Alternatively, a second anodization process can be carried out to consume part of Al metal film, so that the barrier layer and top porous $Al_2O_3$ layer are above the Al metal layer.

Figure 5A:
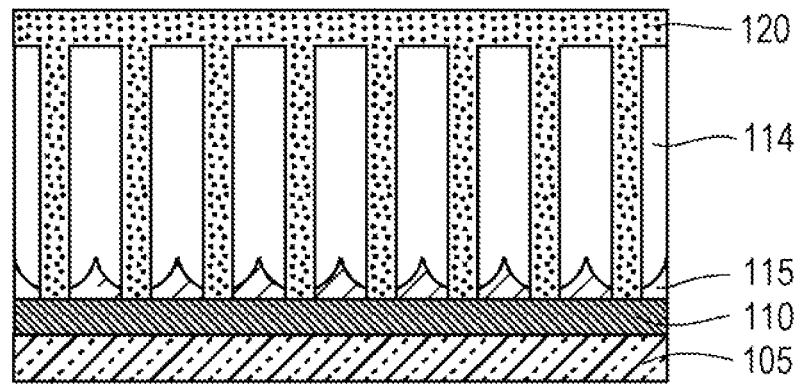
FIGS. 5A and 5B show respectively a noble metal deposited on top of the nano-structured surface then followed by removing the noble metal film from the top layer.
Figure 5B:
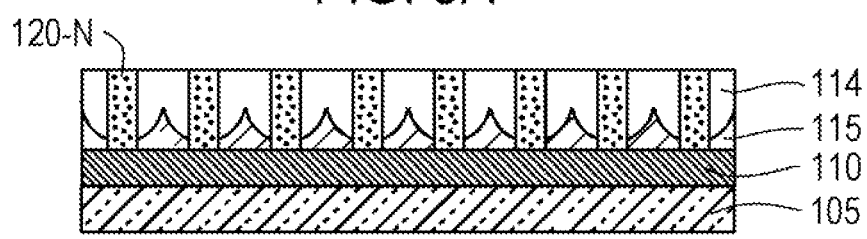
Figure 6:
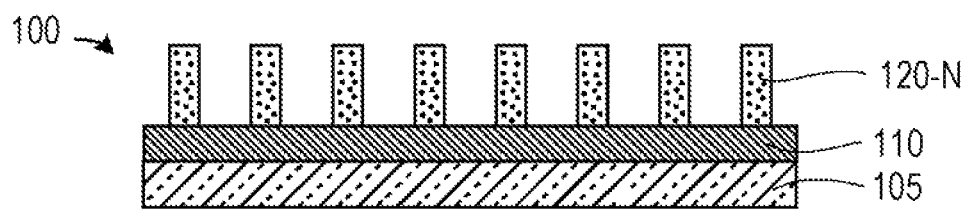
FIG. 6 shows the side cross sectional view of the nano-structured surface with noble metal rods after the oxide layer is removed.

A noble metal, e.g., Ag layer 120 is deposited on top of the porous layer 115 in FIG. 5A and filling the pores 112 by bias PVD process or plating method. In FIG. 5B, the top layer of the noble metal 120 is removed with the noble metal 120-N filled the pores 112. Another wet metal etch or CMP process is carried out to further control height of the noble metal 120-N filling the pores. In FIG. 6 the aluminum oxide 115 and the residue aluminum film 115-AL at the bottom of the porous aluminum layer 115 are removed, then the noble metal rod array with the rod diameter d 120-N left with controlled height (H) and a well-defined nano-structured center to center distance (D) thus completing the fabrication of a noble metal nano-structured surface 100.

The geometries of the masks applied in the above-described fabrication processes are designed to match the expected size of the sensing chip and the area of the metal pad, which locates at the corner of edge of a chip. For field applications, the chemical detection sensing chips are formed as packaged sensing chips by applying different semiconductor packaging technologies, e.g., wire-bonding, flip-chips, tape and rail, system-on chip (SOC), etc.

As disclosed in FIGS. 1-6, this application provides a novel method of using aluminum material and anodization method to creating nano-scaled porous structure on a silicon substrate with a conductive layer of metal coating or other compatible material surfaces. The layer thickness and the novel geometrical parameters of the nano-structure are precisely controllable because the processing parameters of the aluminum PVD, the anodization, and wet etch and the CMP processes are well known in the art. A precisely controllable chemical etching process is applied to remove the barrier layer at the bottom surface of the pores. The porous aluminum oxide layer is applied as a hard mask for depositing the noble metal into the pores 114 and then the residue aluminum film and the porous aluminum oxide are removed to expose the noble metal rods with well-controlled height H and distance D between the rods by controlling the anodizing processes on the aluminum layer, the chemical process, or the CMP processes. The present application thus provides a nano-structured surface fabricated by these novel processing steps on a (100) silicon substrate. By using the nano-structured surface, a Raman scattering band around 520 $cm^{-1}$ from silicon substrate can be applied as the internal reference to assist alignment during Raman experiment and calibrate spectrum frequency and intensity in the field application. A voltage may be applied to the nano-structure sensing surface through the conductive layer 110 for the purpose of attracting electrically charged trace chemical in the form of electrically charged molecular clusters, e.g., either negatively or positively charged particles depending on the sensing applications. Furthermore, the conductive layer 110 can also be cooled to a lower temperature below a normal room temperature to further enhance surface adsorption of molecules of interest.

Figure 7A:
FIGS. 7A to 7H are a series of cross sectional views and top views to show an alternate processing method to form nano-structure surface in accordance with the present application.
Figure 7D:
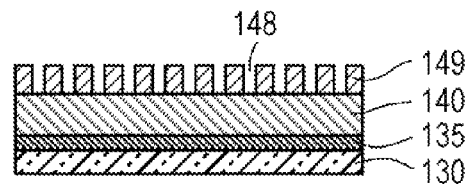
Figure 7B:
Figure 7G:
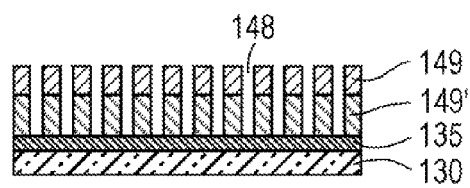
Figure 7C:
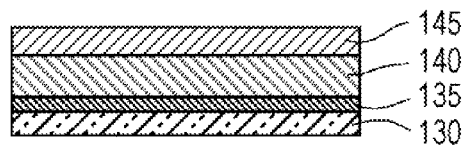
Figure 7H:
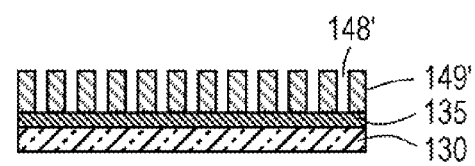
Figure 7F:
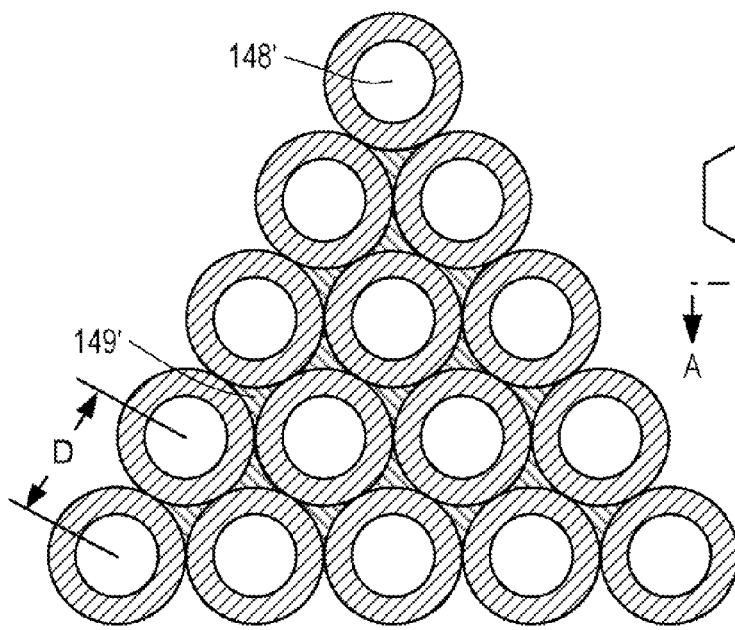
Figure 7E:
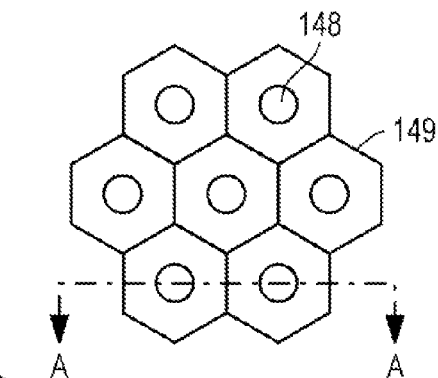

Referring to FIGS. 7A to 7F for a series of processing steps to fabricate another nano-structured noble metal surface of this application, FIG. 7A shows a two-layer structure. The two-layer structure has an electrically and thermally conductive layer 135 deposited on top of a silicon substrate 130. In some embodiments, the conductive layer 135 may be titanium (Ti) or nickel (Ni) layer. The substrate 130 may be a n-type silicon substrate (3-8 $\Omega$-cm) or oxidized (30-50 nm $SiO_2$) p-type silicon wafers (5-10 m$\Omega$-cm). The thickness of this conductive metal film 135 is usually controlled in the range of 100 Å-1,000 Å and optimized to provide best adhesion to a noble metal layer, e.g., a silver (Ag) layer, that can be subsequently deposited. The thickness of the metal layer 135 is also optimized for applying an electrical bias to the sensing surface for trace chemical detection and further for applying a lower temperature to the sensing surface to enhance sensitivity of trace chemical detection. In FIG. 7B, a noble metal layer 140 is deposited on top of the conductive layer 135. The noble metal may be a silver layer, e.g., Ag layer having a thickness of 0.5-5,000 nm, or 10-200 nm. In FIG. 7C, a second metal layer 145, e.g., an aluminum layer with a purity of 99.999% with a thickness in the range of 1.0-10.0 micrometers, is deposited on top of the noble metal layer 140. In FIG. 7D an anodization process is carried out to produce a porous structure in a form of porous aluminum oxide 145'. A top view is shown in FIG. 7E where the porous structure is formed with naturally self-assembled hexagon-shaped nano pore-array that includes a plurality of pores 148 surrounded by hexagon-shaped pore wall 149. After removing top anodized layer and the barrier layer by a wet chemical process, a second anodization process is carried out to consume all Al metal so that the barrier layer and top porous $Al_2O_3$ layer 145' are right above the noble metal layer 140. Then a wet etch process is performed to widen the pores 148 and to remove the barrier layer at the bottom of the pores 148. As that shown in FIG. 7F, as the wet etch process proceeds, the pores 148 are widened and the walls 149 surrounding the pore become thinner. The etch process can be controlled to either form a plurality of nano-holes 148 surrounded by wall 149 or the pores 148 can be widen such that the pores 148 tangentially touch each other. After the completion of the etch process, a plurality of quasi-triangle columns 149' can be formed as plurality of nano-rods.

In FIG. 7G, the noble metal layer 140 is etched down and the pores 148 are extended downward to reach the conductive titanium layer 135. In FIG. 7H, a wet oxide etch is performed to remove the aluminum oxide followed by a wet metal etch to remove the aluminum residue at the bottom of the pores 148. The aluminum oxide 115 and the residue aluminum film 115-AL at the bottom of the porous aluminum layer 115 are removed with noble metal rod array 149' left with controlled height (H), nano-rod diameter (d) and a well-defined structured distance (D) between the rods thus completing the fabrication of a noble metal nano-structured surface 100 with quasi-triangle nano rods distributed as triangle array.

This method results in nano rods 149' with quasi-triangle shape. The coordination number is three. The advantages of this method over the embodiment shown in FIGS. 1 to 6 as that discussed above are i) better film adhesion between the Ti layer 135 and the Ag layer 140, ii) shorter inter-nano-rod distance, i.e., $D_A$ as shown in FIG. 7F, with about 40% reduction comparing to $D_B$ if all other process conditions are the same, iii) the height of the nano rods 149' can be well-controlled by Ag PVD in film thickness through the whole wafer containing at least several hundred or even several thousand devices.

According to above descriptions, the self-assembled nano sensing surface is formed that the Ag triangle nano-rod array 149' or hexagonal nano-hole array 148' wherein each Ag nano-rod or nano-hole array are spatially isolated from each other.

The nano-rod array dimension size can be well controlled by processes mentioned above. Specifically, the array dimension and size are well controlled within the ranges as set forth below:

| | |
|---|---|
| 1) Ti film thickness: | 5-5,000 nm |
| 2) A width of the nano rod diameter, d: | 0.5-500 nm |
| 3) Nano rod inter-particle distance, D: | 0.5-1000 nm |
| 4) Nano rod height, H: | 0.5-1000 nm | wherein d is a width, that is, a lateral dimension of the nano rod. For example, d can be the diameter of a substantially round nano rod. In another example, d can be a width of substantially rectangular nano rod.

On the other hand, the nano-hole array dimension and size can be well controlled by processes mentioned above. Specifically:

| | |
|---|---|
| 1) Ti film thickness: | 5-5,000 nm |
| 2) A width of the nano hole diameter, d: | 0.5-500 nm |
| 3) Nano hole inter-hole distance, D: | 0.5-1000 nm |
| 4) Nano hole depth: | 0.5-1000 nm | wherein d is a width, that is, a lateral dimension of the nano hole. For example, d can be the diameter of a substantially round nano hole. In another example, d can be a width of substantially rectangular nano hole.

Figure 8:
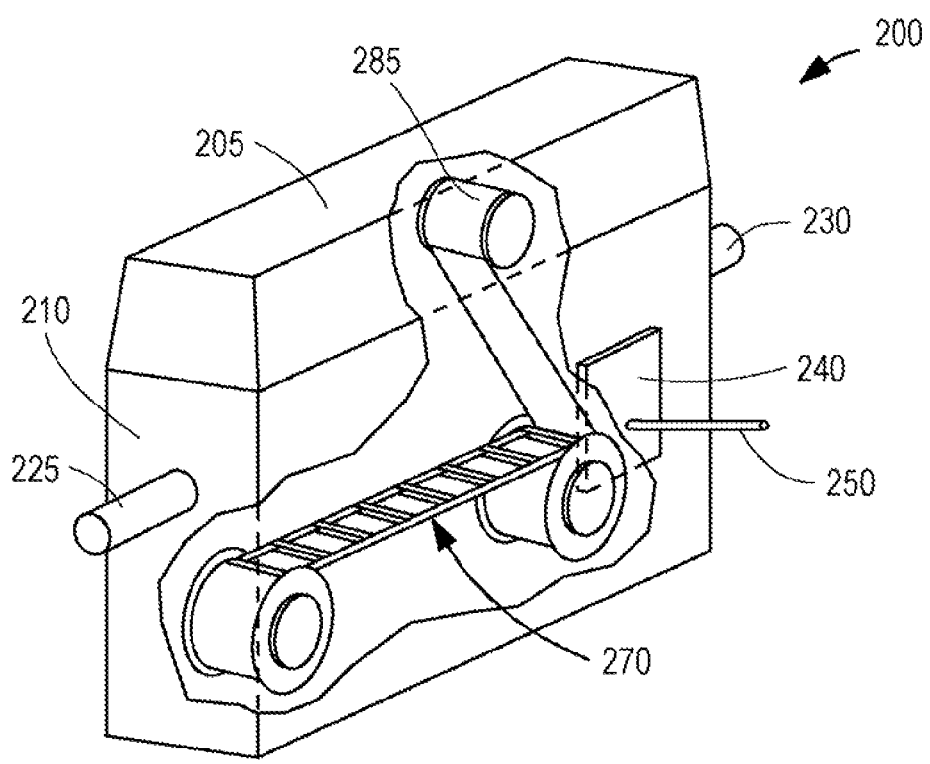
FIG. 8 is a perspective view for showing a SERS or SERRS probe contained in air tight sealed probe cell.
Figure 9:
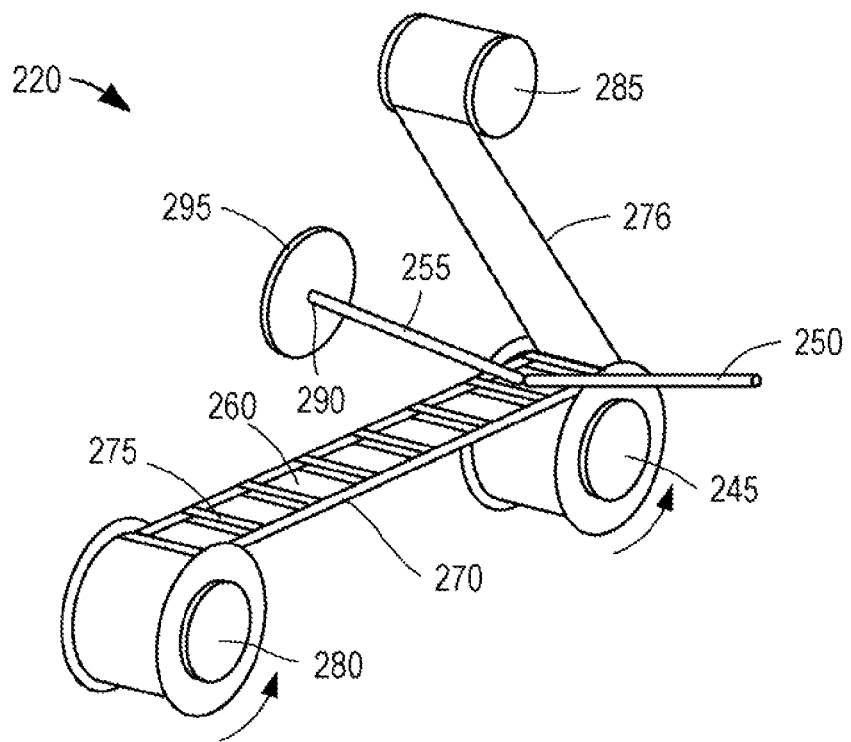
FIG. 9 is a perspective view for showing a roller for moving and exposing the nano-structured sensing surface to incident laser beam as implemented in a SERS or SERRS probe of FIG. 7.

The nano-structured sensing surface provided with noble metallic nano-rods as shown in FIGS. 6 and 7H can be implemented to fabricate the probe cells as shown in FIG. 8. Referring to FIG. 8 for a SERS or SERRS probe 200 of this application implemented as a Raman scattering sensor. The probe 200 includes an airtight cell 210 covered by a housing cover 205. The airtight cell 210 encloses a mechanism 220 with further structure details shown in FIG. 9 below. The cell 210 includes an air outlet 225 connected to a vacuum pump (not shown) to generate a vacuum space inside the cell 210. The cell further includes an air inlet 230 that has a valve to intake sample molecules as sniff trace chemicals for adsorbing onto the nano-structured surface as shown in FIG. 9. The probe 200 further includes an optical window 240 and a lens 250 for projecting laser beam as an incident beam to strike on the nano-structured surface to generate a scattering signal to carry out a light scattering molecule detection operation. The airtight cell 210 thus provides an isolated space as a mini-environment for light scattering measurement.

FIG. 9 is a perspective view of a mechanism 220 for supporting and operating the nano-structure surface that is fabricated with noble metal nano rods 120-N as shown in FIG. 6. The purpose of the nano-structured surface roller is to provide a mechanism to expose a fresh nano-structured surface 100, (one pocket size) to the air molecules inside the probe cell for any trace chemical molecules to adsorb onto the surface to provide surface-enhanced Raman scattering when laser light strikes on the surface. A nano-structured surface 260 can sense trace chemicals. The nano-structured surface 260 can be fabricated with photolithographic method, e-beam lithographic method, chemical reaction, PSL layer deposition followed by metal deposition, or special VLSI technology as described above. For example, the nano-structured surface 260 is compatible with nano-structured surface 100 described above and the nano holes and nano rods disclosed in relation to FIGS. 13A to 15D. The nano-scaled noble metal particles are fabricated on a flexible metal foil or polymer material 707. To prevent the sensing surface from unexpected adsorbing molecules from air, the sensing surface is covered with a polymer or thin metal film 276. Further, to allow only a small portion of the surface to be exposed to intended sample molecules, the surface is structured such that each small area is surrounded with a circle, squared, rectangular, or any other type of shapes with sealing ridges 275. When a new measurement is to be made after sample molecules are pumped into the probe cell, the driving roller 280 and the thin film peel roller 285 can advance a distance equal to the sealed pocket size to peel off the thin film 276 cover and expose the fresh nano-structured surface 260 for molecules to adsorb onto it. The rollers 245, 280 rotate in the direction as shown by the arrows on the rollers 245, 280. The laser beam 250 enters the cell through an optical window and strikes the nano-structured surface 260. The reflected spectral light 255 is reflected off the exiting path by a reflecting mirror 290. The scattered light is collected by the objective lens 295.

Figure 10:
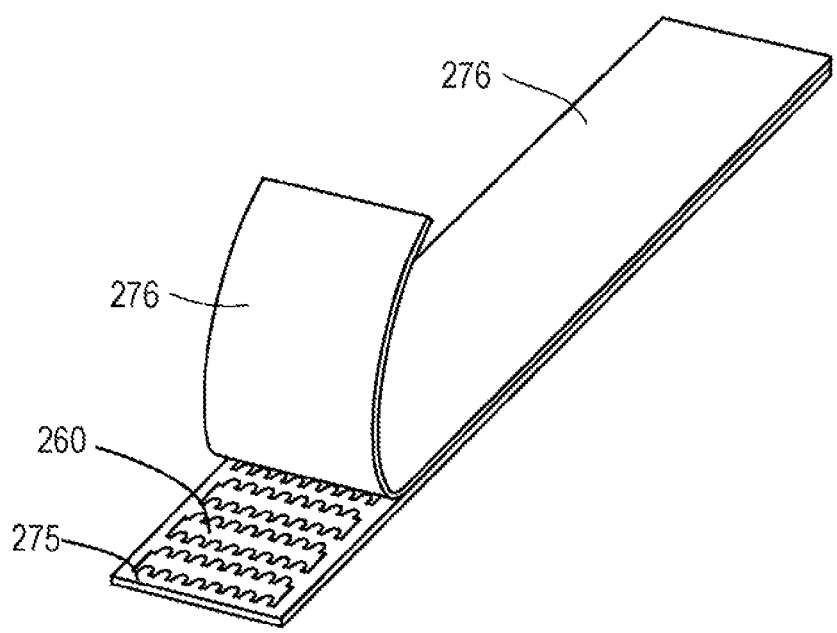
FIG. 10 is a perspective view for showing the surface packaging configuration of the nano-structured surface.

Referring to FIG. 10 for the structural details of the sealing ridges 275 surrounding and securing the nano-structured surface 260 in a pocket. In exposing the nano-structured surface 260 to the incident light 250, the thin film 276 is peeled off to allow the nano-structured surface 260 to receive the incident laser beam and to allow interested trace chemicals adsorbed onto the fresh sensing surface to generate a Raman scattering light for trace chemical detection. The peeling-off configuration and sensing process enable the trace chemical detection operation to effectively minimize sample contamination and allow a new detection operation to conveniently carry out every trace chemical measurement by applying a fresh nano structured surface.

Referring to FIGS. 9 and 10 again, the scattered light can be collected by a lens 295 before exiting the probe cell through the exit window (not shown). The scattered light can be analyzed by a Raman spectrometer to produce a Raman spectrum. A mirror 290 can direct a reflected laser beam 255 away from the exit window to prevent the reflected laser beam 255 to add noise in the Raman scattering signal.

To enhance the molecular adsorption of the metal surface, a DC voltage source is provided and connected to the sensing surface to provide a positive or negative voltage on the surface (not shown in the figures). Controlling the voltage can selectively enhance certain molecular adsorption; thus, provide a biased in mechanism to enhance Raman scattering signals for certain molecules of interest. Furthermore, in order to enhance the molecular adsorption of nano-structured sensing surface, a thermoelectric cooler is applied to cool sensing surface down to the region from 0° C. to 20° C., which many trace chemicals of interest are condensed onto the sensing substrate in this temperature region, so that to further maximize trace chemical molecules to adsorb onto the sensing surface, and that further effectively enhance the Raman scattering signal.

To further enhance Raman scattering signal from a nano-structured sensing surface, a polarized laser beam is applied, which either close to parallel to the sensing surface and/or one of the principal axes of the nano array, or close to perpendicular to the sensing surface. The incident angle of the laser beam is arranged such that the laser polarization direction is closely aligned to the nano rods axis direction, i.e., perpendicular to the sensing surface normal direction, or parallel to the sensing surface. Since many organic chemical molecules are of benzene-ring contained structure, such chemical molecules are expected to orient with its large ring structure that can be conveniently polarized for laying flatly on nano-rod edge surface, nano-rod top surface, or bottom surface between neighboring nano-rods.

To reduce Raman scattering noise, the voltage applied to the metal surface can be modulated with a known frequency to provide a mechanism for differential measurement, as described in more detail below.

Figure 11:
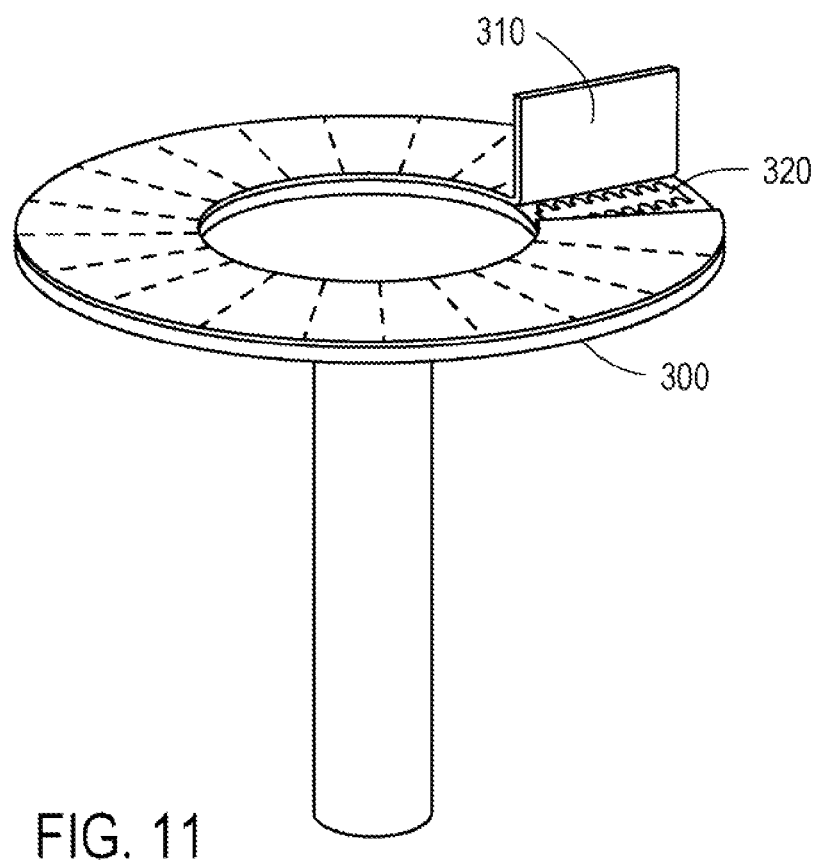
FIG. 11 is an alternate embodiment with a nano-structured surface with pocket sealed and disposed as thin film on a rotary wheel.

An alternative embodiment of the nano-structured noble metal surface roller is illustrated in FIG. 11. In this embodiment, a rotary wheel 300 is constructed to provide pocket of nano-structured surface for SERS or SERRS. The wheel is motorized (not shown in the figure) and controlled by an electro-mechanical device. Each time sample air is pumped into the probe cell, the motorized wheel can rotate a step while the covering thin film 310 is lifted to expose the pocket surface 320. A number of pockets can be fabricated on the wheel to provide multiple measurements without changing any parts. Similar to the embodiment shown in FIG. 9, a DC voltage is connected to the metal surface to provide a positive or negative voltage for surface adsorption enhancement. The mechanism for exposing the nano-structured surface sealed in each individual pocket is similar to that of a roller driven one as described in previous paragraphs. The wheel 300 is enclosed inside the probe cell. The laser beam strikes the surface that is exposed to sample air and reflects off from the surface. As described above, the reflected spectral light is directed away from the light dispersing and collecting optics. Only the scattering light is dispersed and imaged to a CCD camera for spectral analysis.

The SERS or SERRS detector, as disclosed above has a compact size enclosed in an airtight probe cell with a nano-structured sensing surface, configured for individual exposure. The probe as disclosed can be conveniently deployed in the field. The nano-structured surface is configured and partitioned as pocketed and film protected surface for very cost effective and economical implementations. The nano-structured sensing surface is covered under the film and therefore is protected from contamination before a trace chemical detection is performed. The ridges are effectively implemented to seal and securely attach the protective film onto the nano-structured surface to assure the nano-structured surface is free from contaminations. A mechanism is disclosed to lift the covering film to expose a small portion of the surface to sample and detect the molecules. The rollers as disclosed support and operate the nano-structured surface to expose only a single pocket at a time to control an accurate and effective operation of the detection processes. Also, the detection operation is performed with a continuously advanced fresh, uncontaminated surface for new SERS or SERRS measurement. The roller configuration further enhanced the film replacement process for more efficient chemical detection operations. The DC voltage as now applied to the nano-structured surface further enhances the adsorptions and sensitivity of trace chemical detection. In some embodiments, the voltage applied to the conductive layer supports the nano-structured surface can be modulated to provide a differential signal to further reduce noises. To enhance the molecular adsorption of nano-structured sensing surface, a thermoelectric cooler is applied to cool sensing surface down to the region from 0° C. to 20° C., which many trace chemicals of interest are condensed onto the sensing substrate with higher probability in this temperature region. Furthermore, in order to enhance the molecular adsorption of nano-structured sensing surface, a polarized laser beam is applied, either parallel to the sensing surface and/or one of the principal axes of the nano array, or perpendicular to the sensing surface.

This application further discloses additional methods of carrying out a chromatography operation, e.g., gas chromatography (GC) or a high-performance liquid chromatography (HPLC) operation, before a trace chemical sensing is performed. A chromatography process is a process to separate a mixture by distribution of the components of the mixture between a mobile and a stationary phase over time. The mobile phase may be a liquid or gas phase and the stationary phase may be a component attached to a column packing material. This application thus discloses a combined GC-Raman (or GC-SERS) sensing system or a combined HPLC-Raman (or HPLC-SERS) sensing system by first carrying out a classification by phase process, such as GC or HPLC, followed by detecting the trace chemicals by Raman scattering sensing process described above.

The detection sensitivity of the Raman scattering sensors can also be enhanced by that the surface electron-photon coupling effect and surface interference effect can be combined with the dimension of the nano-structured surface. Specifically, the electron mean-free path (MFP) on a gold or silver surface is about ten to fifty nano-meters as disclosed by Penn, D. R. in 1976 Phys. Rev. B13, 5248 and the Universal Curve (Physics at Surface, Andrew Zangwill, Cambridge University Press, 1988). The silver metal surface can be configured to have a nano-array with the scale to match the scale of the silver electron MFP. The physical properties of the silver nano-structured surface array demonstrate sudden significant changes when interacted with an incident visible polarized laser. The sudden changes of the physical properties can be quantified to correlate to the interaction between the photons and the electrons and other sub-atomic particles caused by the surface electron-photon-phonon coupling effect, surface interference effect, surface resonance effect, quasi-diffraction effect at the surface, an so on.

A MFP of an electron on a silver nano-structured surface is based on the Universal Curve as a function of the kinetic energy of that electron as tabulated below. Assuming the excited laser energy is transferred as kinetic energy to an electron on the Ag surface, the table below lists the MFP of the electron on a silver nano-structured surface for different laser wavelengths:

| | | | |
|---|---|---|---|
| a) | laser wavelength = 375 nm, | MFP ≈ | 50 Å |
| b) | 532 nm | | 100 Å |
| c) | 785 nm | | 220 Å |
| d) | 1064 nm | | 410 Å |

Accordingly, the electron MFP at the Ag metal surface is in the range of 5-50 nm under the condition that the excited laser wavelength is in the range of 375-1064 nm. From above discussion, it can predict that the optimized and maximized SERS signal enhancement occurs under the condition that when the electron MFP is functionally matched by optimized several nano-structure parameters. These parameters include i) the diameter of the silver nano rod array or nano hole array d, ii) The inter-rod or the inter-hole distance on the nano-structured surface D, iii) the height of the nano rod array, or the depth of the nano hole array, or iv) any two of the above three parameters. The "functionally match" as described above may include the condition that Ag surface nano feature size(s) mentioned above is(are) approximately equal to, smaller than, integer numbers of, or with a special mathematical function to the estimated electron MFP of Ag metal. The functional match correlation can also be defined as by a functional relationship as characterized by the interaction between the photons and the electrons and other sub-atomic particles caused by the surface electron-photon coupling effect, surface interference effect, surface resonance effect, quasi-diffraction effect at the surface, an other inter-particle interactions.

Similarly, above MFP of Ag electrons match Ag metal surface nano feature size(s) can be extended to i) The Electron Wavelength. Consider that the electron wavelength is in the range of about 2 Å-200 Å at the surface of Ag metal, if the metal surface nano feature size matches that range, then, non-conventional physical phenomena may occur under that laser beam excitation, such as surface enhanced Raman scattering, then resulted Raman scattering can be significantly enhanced. ii) The Phonon Wavelength. Consider that the phonon wavelength is in the range of 2 Å-1,000 Å at the surface of Ag solid, if the metal surface nano feature size matches that range under the laser excitation, then Raman scattering can be significantly enhanced. It should be noted that the phonons are defined as the quanta of energy of the normal vibrational modes of a crystal lattice or chemical bonding, and Raman spectrum records crystal lattice or chemical bonding vibration. iii) The Phonon Mean-Free Path. Consider that the phonon mean free path is in the range of about 2 Å-20 μm at the surface of Ag solid, if the metal surface nano feature size matches above range, then resulted Raman scattering can be significantly enhanced. Notice that the phonons are defined as the quanta of energy of the normal vibrational modes of a crystal lattice or chemical bonding, and Raman spectrum records crystal lattice or chemical bonding vibration. Then Raman scattering can be significantly enhanced by the interaction among the photons, the electrons, the phonon, and other sub-atomic particles caused by the surface electron-photon-phonon coupling effect, surface electro-optical interference effect, surface resonance effect, quasi-diffraction effect at the surface, an other inter-particle interactions.

Based on the above descriptions, considering the interaction between the incident laser and the nano-structured surface, the scattering sensing intensity can be further enhanced by applying the incident laser modulation to adjust the incident laser to have a glance incident angle such that the laser polarization direction is close to the direction of the nano-rod axis, i.e., perpendicular to the sensing surface or parallel to a sensing surface. The sensing performance can also be enhanced by shifting the wavelength of the excited laser with about half of Raman band width and applying a spectra difference analysis technique to filter out a large portion of the background noises or/and unwanted fluorescence signal from sample, sensing environmental and sensing system, which both are with very broad band width. In addition to the above techniques, an alternate method is an electronic signal differential method to further enhance the performance of the scattering sensing process by shifting the charged-couple device (CCD) detection pixel position then applying a spectra difference method to reduce noises of detection.

Figure 12A:
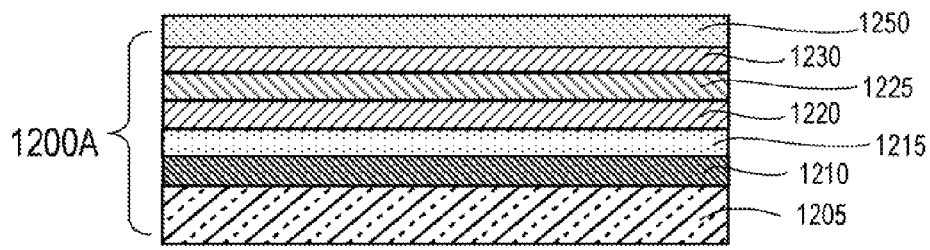
FIGS. 12A-12C are cross-sectional views of multi-layer structures from which nano structures can be built.

In some embodiments, nano structures such as nano holes or nano rods can include multiple layers in their structures. Referring to FIGS. 12A, a multi-layer structure 1200A can include a substrate 1205, an adhesion layer 1210, structure layers 1215, 1220, 1225, 1230, and an upper layer 1250. The substrate 1205 can include a silicon substrate having an (100) or an (111) crystal plane orientation. The adhesion layer 1210 can for example include a conductive material that can include Ti, Ni, or Co. The adhesion layer 1210 can be formed by physical vapor deposition (PVD) on the substrate 1205. The adhesion layer 1210 can be electrically conductive, thermally conductive, or both electrically and thermally conductive. An exemplified thickness for the adhesion layer 1210 is 5-5,000 nm, such as 10 nm to 100 nm.

The adhesion layer 1210 can provide several functions. It can provide adhesion to the substrate 1205. It can provide an electrical bias or a temperature bias to the nano structures to be formed to enhance to light scattering signal. It can also act as a thermal heat sink. During the fabrication, the adhesion layer 1210 can act as a stop layer for chemical etching (as described below) or a diffusion barrier layer.

An optional thermal bias layer 1215 can next be formed on the adhesion layer 1210. The thermal bias layer 1215 can be formed for example by PVD. The thermal bias layer 1215 can be made of Cr, Pt, Ru, a Ni—Cr alloy, NiCrN, a Pt—Rh alloy, a Cu—Au—Co alloy, an Ir—Rh alloy, or a W—Re alloy. The thickness of the thermal bias layer 1215 can be in the range of 5 nm to 10 μm, such as 10 nm to 1 μm. The thermal bias layer 1215 can perform different functions depending on the applications. For example, when the nano holes or nano rods are used for sensing trace chemicals in a Raman scattering, the thermal bias layer can be cooled to act as a heat sink for the nano holes or nano rods. Lower temperature can enhance the adsorption of the trace chemicals to the surfaces of the nano holes or nano rods. The thermal bias layer 1215 can also be heated after each chemical sensing measurement to release the molecules adsorbed on the surfaces of the nano structures such that the nano surfaces can be reused for the next chemical sensing measurement.

In some embodiments, the adhesion layer 1210 and the thermal bias layer 1215 can be formed by a single substantially uniform layer, which for example can be implemented by a layer of Ti or Ni.

Next structure layers 1220, 1225, and 1230 can be formed on the thermal bias layer 1215. The structure layers 1220, 1225, and 1230 can have different material compositions A, B, C (thus the structure layers can be abbreviated by "ABC"). Alternatively, the structure layers 1220 and 1230 can have a same material composition "A" and the structure layer 1225 can have a different material composition "B" (the structure layers can be abbreviated by "ABA").

Figure 12B:
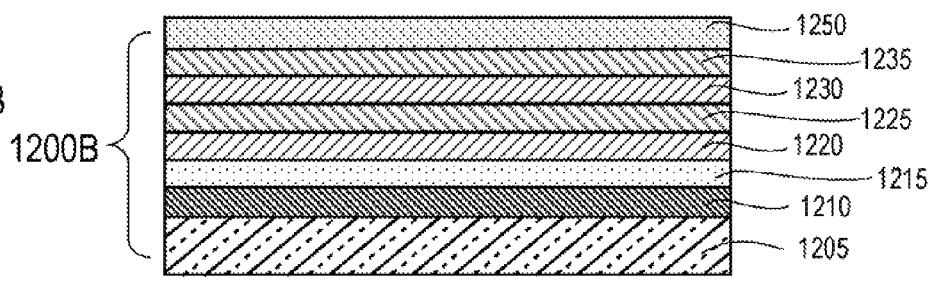
Figure 12C:
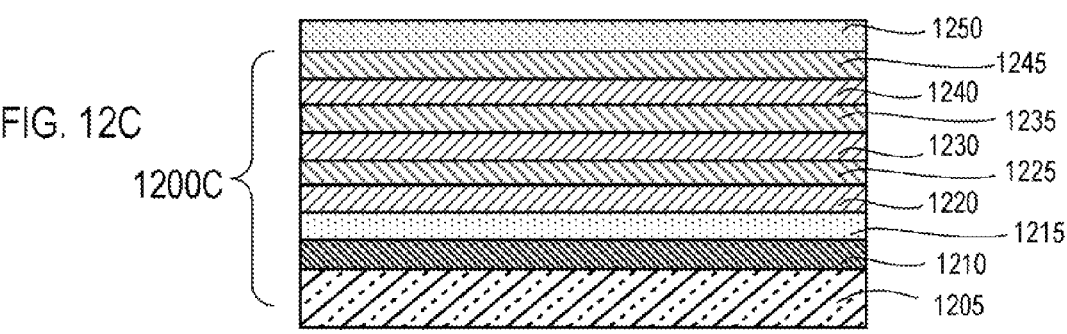

Similarly, referring to FIG. 12B, the structure layers 1220-1235 can include three or more layers having different sequences such as "ABAB", "ABAC", "ABCA", "ABCB", and "ABCD", etc., wherein "A", "B", "C", and "D" each represents a different material composition. Additional, referring to FIG. 12C, the structure layers 1220-1245 can have different material sequences such as "ABCDEF", "ABABAB", "ABCABC", etc., wherein "A", "B", "C", "D", "E", "F" each represents a different material composition. The multi-layer structure can have a layer sequence of $(AB)_n$, $(AB)_nA$, $(ABC)n$, $(ABC)_nA$, $(ABC)_nAB$, etc., in which n is an integer.

The structure layer 1220, 1225, 1230 ... 1245 can include metallic materials such as Ag, Au, Cu, Pt, Al, Fe, Co, Ni, Ru, Rh, and Pd; Ag doped with chlorine or chloride and Au doped with chlorine or chloride; oxides such as $TiO_2$, $SiO_2$, $Al_2O_3$, $Si_3N_4$, $Ta_2O_5$, Zn oxide, Sn oxide, Sb oxide, Ag oxide, Au oxide; and polymeric materials such as Ethylene Chlorotrifluorethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP). The structure layer 1220, 1225, 1230 ... 1245 can also include semiconductor materials such as GaAs, ZnS, ZnO, CdS, $Er^3$ in $SiO_2$, InGaN, InGaN/GaN, AlGaAs, InAgAs, GaAs/GaAlAs, GaN, 4H SiC, AlN, GaN, AlGAn/GaN, InP, InAlAs/InGaAs, Cs, Rb, diamond, InAs, AlSb/InAs, AlGaAs/InGaAs, InAlAs, InGaP, SiGe, Al, Si, C, etc.

The structure layer 1220, 1225, 1230 ... 1245 can have a thickness in the range of 0.3 nm to 2,000 nm. The formations of the structure layer 1220, 1225, 1230 ... 1245 can be implemented by PVD, chemical vapor deposition (CVD), atomic layer deposition (ALD), molecular beam epitaxy (MBE), electrolysis plating, electrolysis plating, spin coating, and spray, which can selected depending on the material composition and applications of the nano structures to be formed.

Next, referring to FIG. 12A, the upper layer 1250 is formed on the structure layer 1230 to complete the multi-layer structure 1200A. The upper layer 1250 can be formed by a material that is adapted to form an impression when printed by a mold. Material suitable for the upper layer 1250 includes polymethyl methacrylate (PMMA). The upper layer 1250 can have a thickness in the range of 20-800 nm, such as 50-350 nm. Similarly, the multi-layer structures 1200B and 1200C can also be formed by respectively forming the upper layer 1250 on the structure layer 1235 and the structure layer 1245.

Figure 13A:
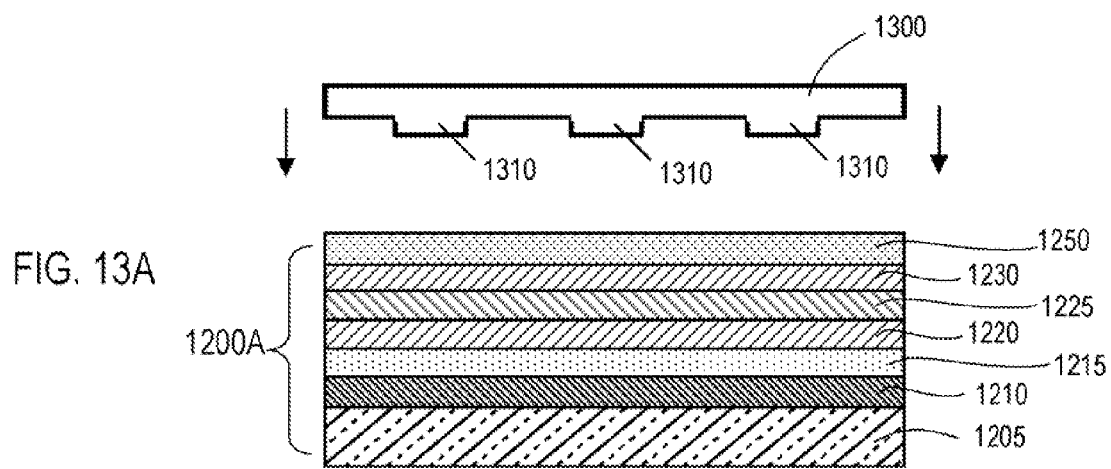
FIG. 13A is a cross-sectional view illustrating the relative positions of a mold and the multi-layer structure of FIG. 12A before imprinting.
Figure 13B:
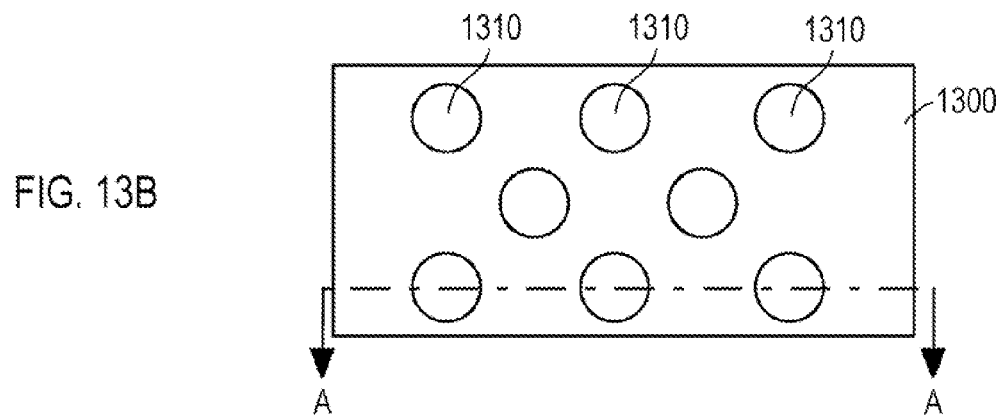
FIG. 13B is a bottom view of the mold of FIG. 3A.
Figure 13C:
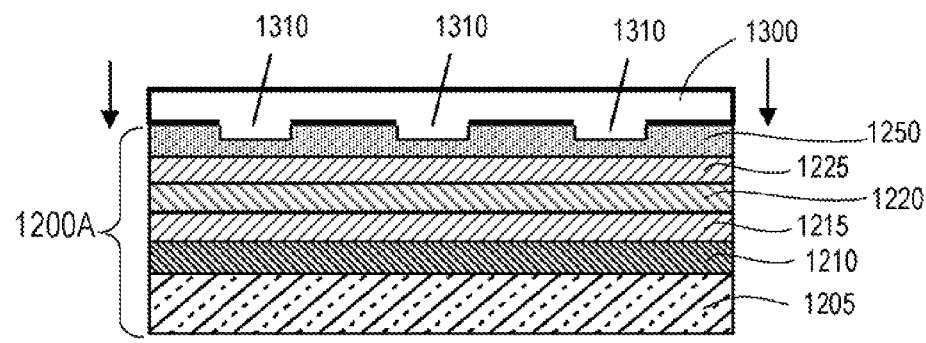
FIG. 13C is a cross-sectional view illustrating the relative positions of the mold and the multi-layer structure of FIG. 12A during imprinting.
Figure 13D:
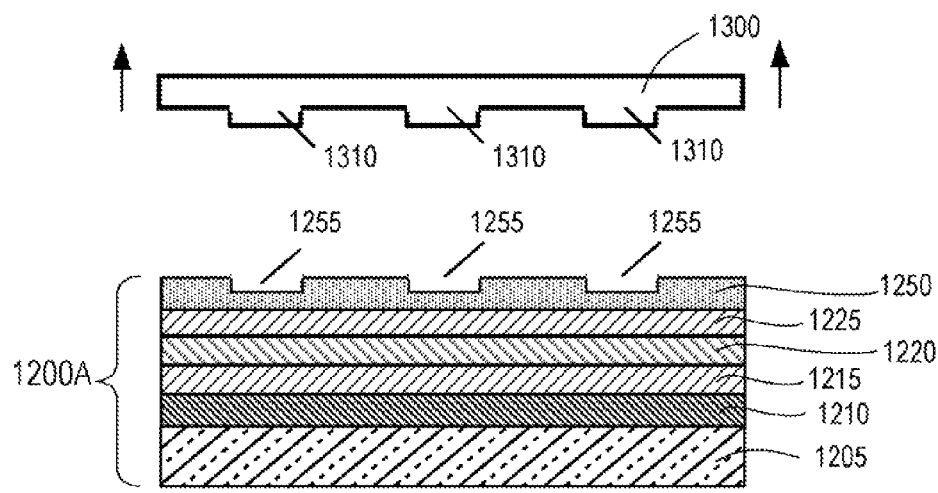
FIG. 13D is a cross-sectional view illustrating the impressions formed on the upper surface of the multi-layer structure of FIG. 12A after imprinting.
Figure 13E:
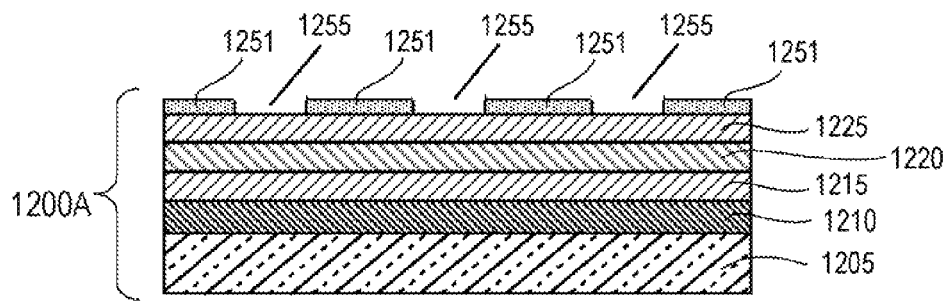
FIG. 13E is a cross-sectional view illustrating the formation of a mask on the multi-layer structure of FIG. 12A.

A mold (template or stamp) 1300, referring to FIGS. 13A and 13B, is next disposed over the multi-layer structure 1200A. The mold 1300 can include a plurality of protrusions 1310 (or holes) facing the upper layer 1250 (the cross section shown in FIG. 13A is along the line A-A in FIG. 13B). The protrusions 1310 (or holes) can determine the shapes and dimensions of the holes (1320) to be formed. The mold 1300 can be made by etching a silicon wafer or Ni or Cr coated glass to produce the protrusions 1310 (or holes) with the proper dimensions and spacing (center to center) in between. The mold 1300 is pressed against the upper layer 1250 as shown in FIG. 13C, to make an impression in the upper layer 1250, as shown in FIGS. 13C and 13D. The impression includes a plurality of recesses 1255 (or protrusions) in the upper layer 1250.

The upper layer 1250 is next chemically etched to form a mask 1251. The upper layer 1250 is etched in the recesses 1255 and the un-imprinted portions. The etching is controlled till the portions of the upper layer 1250 under the recesses 1255 are etch through to form holes 1255 in the mask layer 1251. The upper surface of the structure layer 1225 is exposed in the holes 1255 in the mask 1251.

Figure 13F:
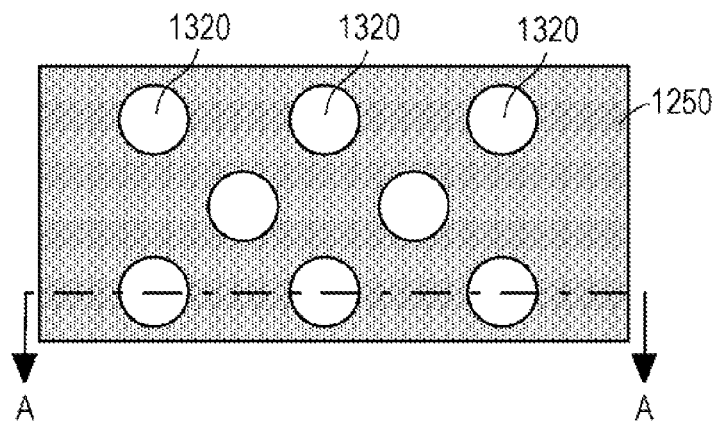
FIG. 13F is a top view of the nano holes formed in the multi-layer structure.
Figure 13G:
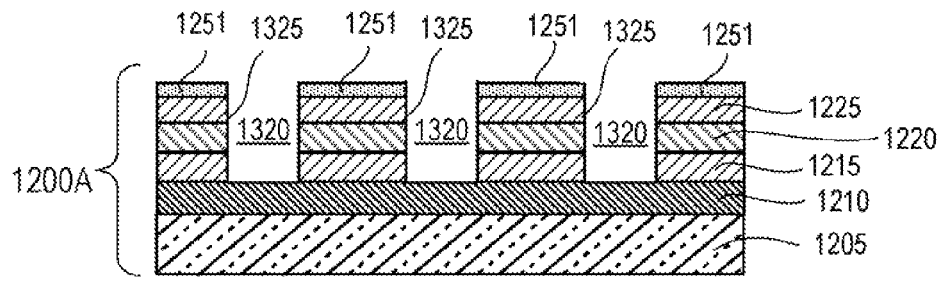
FIG. 13G is a cross-sectional view along the line A-A in FIG. 13F.
Figure 13H:
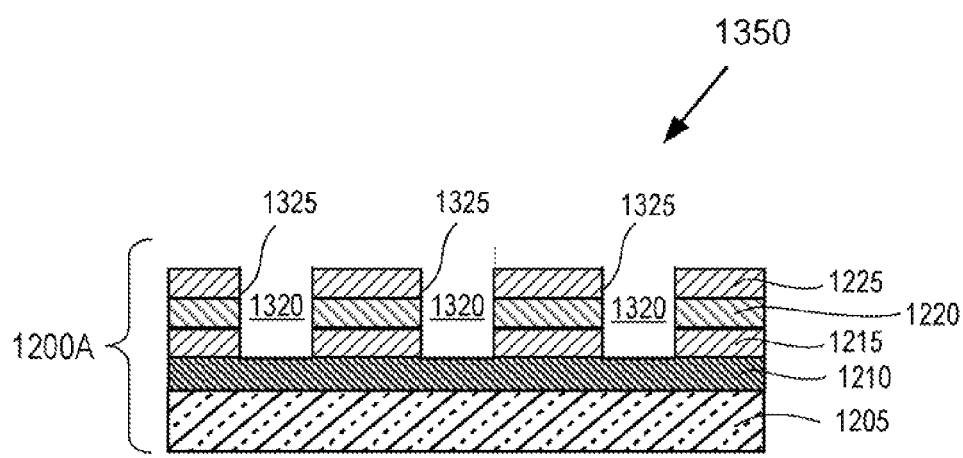
FIG. 13H is a cross-sectional view illustrating the multi-layer structure having the nano holes after the mask is removed.

The structure layers 1215-1225 are next etched by chemical etchant through the holes 1255 to form a plurality of holes 1230 in the multi-layer structure 1200A (FIGS. 13F and 13G). The mask 1251 is subsequently removed to form a multi-layer nano-hole array 1350 having the multi-layer structure 1200A with the plurality of holes 1320 (FIG. 13H). The holes 1320 can have diameters in the range of 0.5-1,000 nm such as 5-200 nm. The center to center spacing between the adjacent holes 1320 is in the range of 0.5-1,000 nm, such as 5-200 nm. At least a portion of the plurality of holes 1320 can be distributed substantially in a periodic array in the structure layers 1215-1225. The holes 1320 include side surfaces 1325 on the structure layers 1215-1225. The surfaces 1325 can be coated by a conductive material. Similarly, the holes can be formed in the multi-layer structures 1200B and 1200C using the steps described above in relation to FIGS. 13A-13H.

The cross-sectional shapes of the holes 1320 are determined by the shapes of the protrusions 1310 in the mold 1300. Examples of the cross-sectional shapes of the holes 1320 can include circles, triangles, rectangles, etc.

Figure 14A:
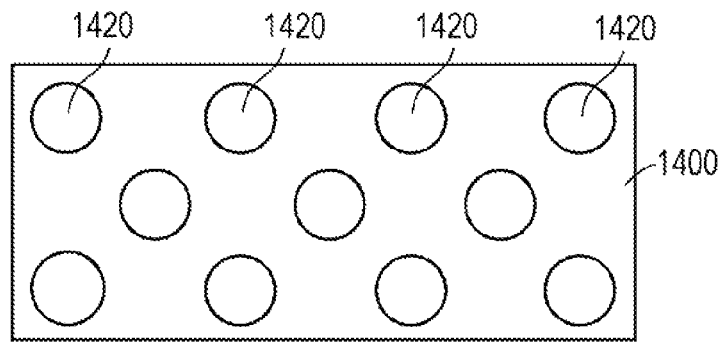
FIG. 14A is a bottom view of a mold for nano-column formation.
Figure 14B:
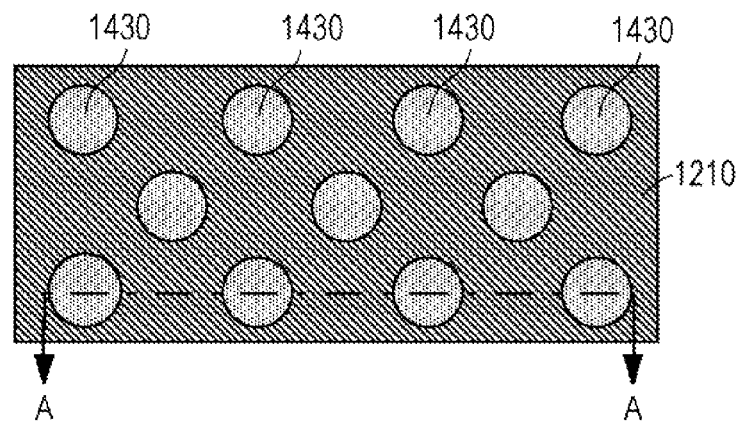
FIG. 14B is a top view of the nano columns of FIG. 14A.
Figure 14C:
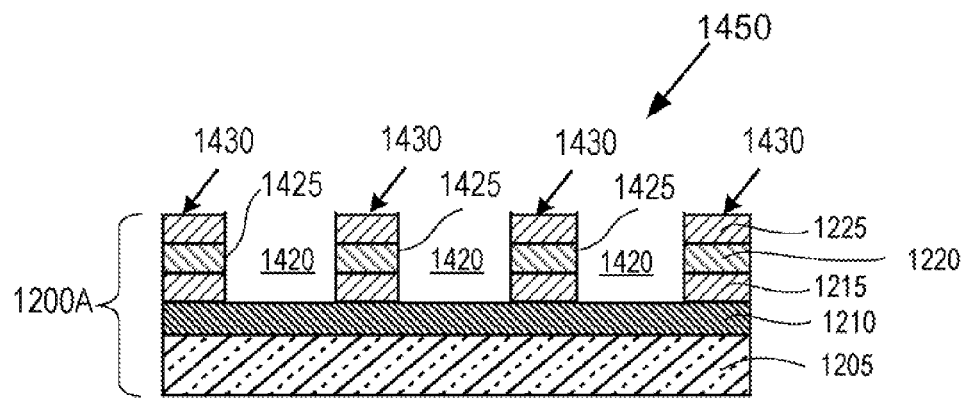
FIG. 14C is a cross-sectional view of the nano columns along the line A-A in FIG. 14B.

In some embodiments, a plurality of columns 1430 can also be formed in the multi-layer structures 1200A, 1200B and 1200C using steps similar to the steps shown in FIGS. 13A-13H. As shown in FIGS. 14A to 14C, a mold 1400 can include a plurality of recesses 1420 or protrusions. The recesses 1420 or protrusions determine the positions and the lateral dimensions of the columns 1430 to be formed in the multi-layer structures 1200A. The mold 1400 can be used to imprint on the upper layer 1250 to produce an impression that has protrusions in the upper layer 1250 at locations where the columns 1430 are to be formed. The multi-layer structure 1200A is then undergone the similar steps of etching, mask formation, and etching the area other than holes or the holes through the mask to form a nano-column or hole array including the plurality of columns 1430 or hole on the adhesion layer 1210, or even down to the substrate 1205 with a depth of 1-10,000 nm. A multi-layer nano column array 1450 is formed. The cross-sectional shapes the columns 1430 are determined by the shapes of the recesses 1420 in the mold 1400. For example, the cross-sectional shapes of the columns 1430 can include circles, triangles, squares, rectangles, rectangles with semi-circle at the both end, ellipse, etc. The diameter d or dimension in X-Y is in the range of 0.3-500 nm, such as 5-200 nm. The spacing (center to center) D between adjacent columns 1430 can be in the range of 0.5 nm-1,000 nm, such as 5-200 nm. The height of the columns can be in the range of 0.5-1,000 nm, such as 5-200 nm. At least a portion of the columns 1430 can be distributed in a substantially periodic pattern.

The disclosed multi-layer nano structure (e.g. the multi-layer nano-hole array 1350 and the multi-layer nano-column array 1450) may enhance the signal of the scattered light in several mechanisms. With the illumination of an incident laser beam, the electron standing waves can be formed in the multiple layers and the substrate, which can enhance surface plasmon resonance and thus Raman scattering. The nano holes or the nano rods can effectively act as nano cavities for the electron resonance. A multi-layer nano structure comprising metal material may also enhance charge transfer between chemical molecules adsorbed onto the surface and the structural materials of the nano rods or nano holes, which can enhance Raman signal. The localized electronic field density (E-field) may also be increased due to the electron resonance in the nano cavities. The strength of Raman scattering signal is known to be proportional to the fourth power of the E-field. Furthermore, the electron standing wave inside the nano cavity may also emit photons which can act as secondary excitation sources. The number of the secondary excitation sources is determined by the number of the nano rods and nano holes in the nano array under an external laser excitation. Lights emitted from the secondary excitation sources can coherently excite the chemical molecules adsorbed onto the sensing surface which may form Raman laser, thus can further enhance Raman signal.

Figure 15A:
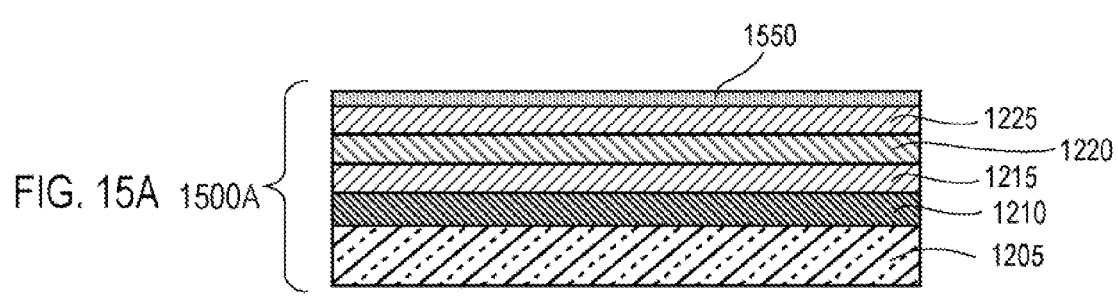
FIG. 15A is a cross-sectional view of a multi-layer structure.
Figure 15B:
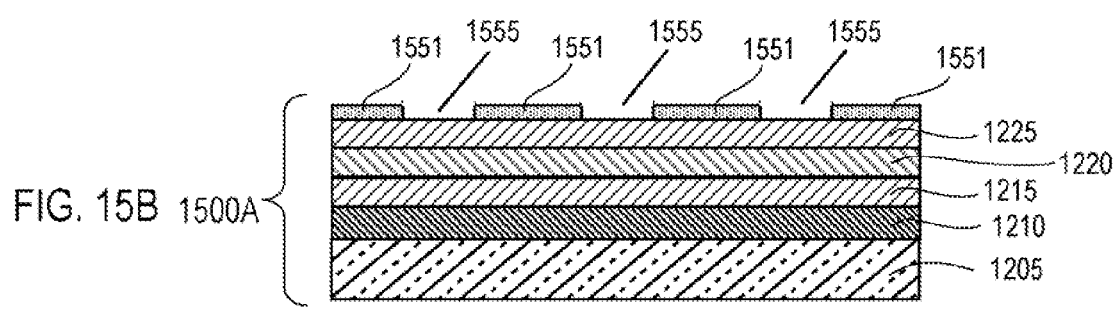
FIG. 15B is a cross-sectional view of the multi-layer structure of FIG. 15A after anodization of the upper layer.
Figure 15C:
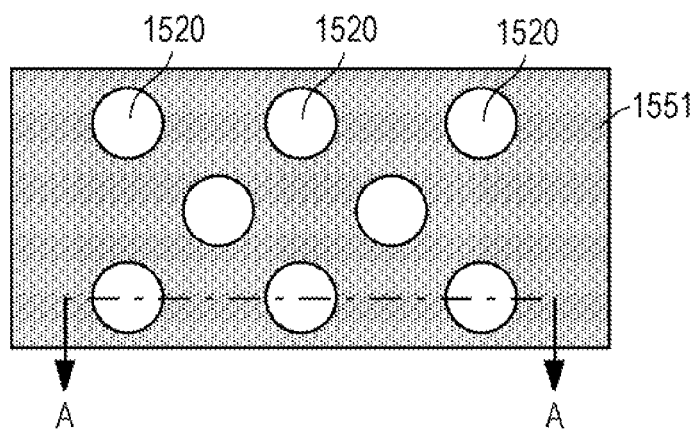
FIG. 15C is a top view of the nano holes formed by etching through a mask formed by the anodization.
Figure 15D:
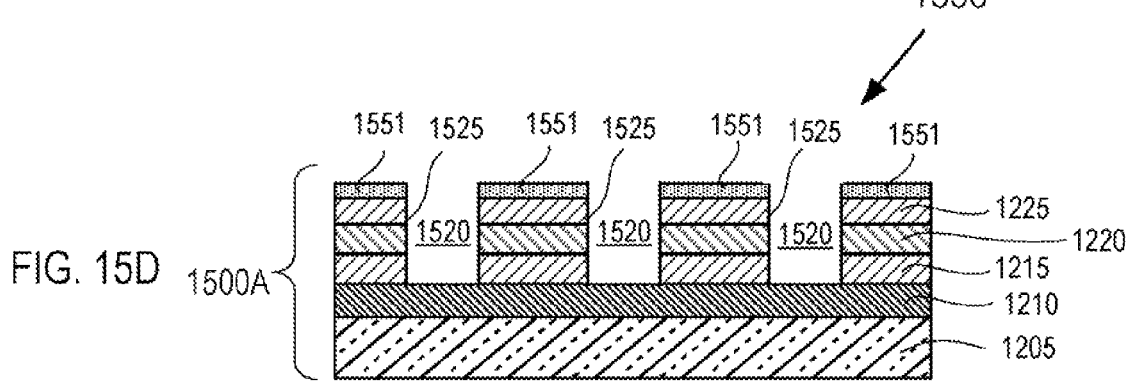
FIG. 15D is a cross-sectional view of nano holes along the line A-A in FIG. 15C.

In some embodiments, a plurality of holes or columns can be formed in a multi-layer structure by etching the multi-layer structure using a mask formed by anodization. As shown in FIG. 15A, a multi-layer structure 1500A includes a same structure as the multi-layer structure 1200A except for an upper layer 1550 is formed on the top (similar to the steps disclosed in relation to FIG. 7C). The upper layer 1550 can be made of a metallic material such as aluminum with a thickness in the range of 0.1-10.0 μm, such as 0.5 to 5 μm. The upper layer 1550 can be anodized using the steps described in relation to FIG. 7D to form pores 1555 in the upper layer 1550. The anodization can involve applying a voltage bias across the upper layer 1550, the adhesion layer 1210 (that is conductive) and the silicon wafer substrate. The aluminum material in the upper layer 1550 can be converted to $Al_2O_3$ in the anodization process. The annealing and the anodization processing parameters can be controlled such as the pores 1555 can self-assemble to form a hexagonal array with targeted physical dimensions in a hard mask layer 1551. The pores 1555 expose the upper surface of the structure layer 1225. The structure layers 1215-1225 are then chemically etched through the pores 1555 in the mask layer 1551 to form a nano-hole array 1550 having a plurality of holes 1520 through the structure layers 1215-1225. The holes 1520 include side surfaces 1525. The mask layer 1551 can optionally be removed after the formation of the holes 1520.

In some embodiments, a mask layer can be formed on a multi-layer structure using a combination of imprinting and anodization methods. For example, a mold having protrusions or recesses can be pressed against the upper layer 1550 in the multi-layer structure 1500A to form an imprinted pattern in the upper layer 1550. A subsequent anodization process can use the recesses in the imprinted pattern as nucleation sites to form the pores 1555 in the upper layer 1550, which produces the mask layer 1551. Alternatively, a subsequent etching process can use the recesses in the imprinted pattern as starting locations to etch the pores 1555 in the upper layer 1550, which produces the mask layer 1551.

It is understood that the layers (e.g. the adhesion layer, the thermal bias layer, and the structural layers) of the multi-layer structures can be formed by different techniques other than PVD. For example, the layers in the multi-layer structures can be formed by chemical vapor deposition (CVD), atomic layer deposition (ALD), molecular beam epitaxy (MBE), electroplating, electrolysis plating, spin coating, and spray.

It is also understood that active devices such as laser and light emitting diode can also be fabricated using the above described systems and methods. Electrode layers can be formed on or below the multilayer structure having the nano holes or nano rods. In some embodiments, a lower electrode layer can be formed by the bias layer or the adhesion. The multilayer rods or holes may have widths in the range of 0.5 nanometer to 10 microns. The center-to-center distances between the adjacent multilayer rods or holes can be in the range of 0.5 nanometer to 10 microns. The depths of the multilayer holes and the heights of the multilayer rods can be in the range of 0.5 nanometer to 10 microns. The number of layers and the thickness of layers can be optimized in accordance with the material used and emission wavelengths.

What is claimed is:

1. A micro structure, comprising:
a silicon substrate;
an adhesion layer on the silicon substrate;
a bias layer on the adhesion layer; and
two or more structure layers on the bias layer, wherein the two or more structure layers comprise different material compositions, wherein the material compositions of the two or more structure layers form a repetitive pattern along the direction normal to the silicon substrate, and wherein the two or more structure layers comprise a plurality of holes through at least two of the two or more of structure layers, wherein widths of the plurality of holes are in the range of 0.5-500 nm, wherein the two or more structure layers comprise four structure layers arranged in a sequence of ABAB, wherein each of the symbols "A" and "B" represents a structure layer having a different material.

2. The micro structure of claim 1, wherein the two or more structure layers comprise a material selected from the group consisting of Ag, Au, Cu, Pt, Al, Fe, Co, Ni, Ru, Rh, Pd, Ag doped with chlorine or chloride, and Au doped with chlorine or chloride.

3. The micro structure of claim 1, wherein the two or more structure layers comprise a material selected from the group consisting of $TiO_2$, $SiO_2$, $Al_2O_3$, $Si_3N_4$, $Ta_2O_5$, Zn oxide, Sn oxide, Sb oxide, Ag oxide, and Au oxide.

4. The micro structure of claim 1, wherein the two or more structure layers comprise a material selected from the group consisting of Ethylene Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP).

5. The micro structure of claim 1, wherein the two or more structure layers comprise a material selected from the group consisting of GaAs, ZnS, ZnO, CdS, $Er^3$ in $SiO_2$, InGaN, InGaN/GaN, AlGaAs, InAgAs, GaAs/GaAlAs, GaN, 4H SiC, AN, GaN, AlGaN/GaN, InP, InAlAs/InGaAs, Cs, Rb, diamond, InAs, AlSb/InAs, AlGaAs/InGaAs, InAlAs, InGaP, SiGe, Al, C, and Si.

6. The micro structure of claim 1, wherein the adhesion layer comprises a metallic material.

7. The micro structure of claim 1, wherein the adhesion layer comprises a material selected from a group consisting of Ti, Ni, Co.

8. The micro structure of claim 1, wherein the bias layer comprises a material selected from a group consisting of Cr, Pt, Ru, a Ni—Cr alloy, NiCrN, a Pt—Rh alloy, a Cu—Au—Co alloy, an Ir—Rh alloy, and a W—Re alloy.

9. The micro structure of claim 1, wherein one or more surfaces in the plurality of holes are configured to adsorb molecules of a trace chemical for detection of the trace chemical using Raman scattering.

10. The micro structure of claim 9, wherein the bias layer is configured to receive a bias voltage to enhance adsorption of molecules on the one or more surfaces in the plurality of holes for Raman scattering sensing of trace chemicals.

11. The micro structure of claim 9, wherein the molecules are adsorbed from a liquid, sol gel, a gas, an aerosol, or a mixture of liquid, sol gel, gas, and aerosol.

12. The micro structure of claim 1, wherein at least some of the plurality of holes are distributed substantially in a periodic array in the two or more structure layers.

13. The micro structure of claim 1, wherein the center-to-center spacing between the adjacent holes in the plurality of holes is in the range of 0.5-1,000 nm.

14. The micro structure of claim 13, wherein the center-to-center spacing between the adjacent holes in the plurality of holes is in the range of 5-200 nm.

15. The micro structure of claim 1, further comprising an upper layer on the two or more structure layers, wherein the plurality of holes intrude through the upper layer.

16. The micro structure of claim 15, wherein the upper layer comprises aluminum or PMMA.

17. The micro structure of claim 1, wherein a width of the plurality of holes are in the range of 5-200 nm.

18. The micro structure of claim 1, wherein the adhesion layer and the bias layer are formed by a single substantially uniform layer.

19. The micro structure of claim 1, wherein depths of the plurality of holes is in the range of 0.5 nm and 1000 nm.

20. A micro structure, comprising:
a silicon substrate;
an adhesion layer on the silicon substrate;
a bias layer on the adhesion layer; and
a plurality of columns on the bias layer, wherein at least one of the plurality of columns comprises two or more structure layers having different material compositions and have widths in the range of in the range of 0.5-500 nm.

21. The micro structure of claim 20, wherein the two or more structure layers comprise three structure layers arranged in a sequence of ABC or ABA, wherein each of the symbols "A", "B", and "C" represents a structure layer having a different material.

22. The micro structure of claim 20, wherein the two or more structure layers comprise four structure layers arranged in a sequence of ABAB, ABAC, ABCA, ABCB, and ABCD, wherein each of the symbols "A", "B", "C" and "D" represents a structure layer having a different material.

23. The micro structure of claim 20, wherein the two or more structure layers comprise a layer sequence of $(AB)_n$, in which "n" is an integer, and the symbols "A" and "B" represent structure layers having different materials.

24. The micro structure of claim 20, wherein the two or more structure layers comprise a material selected from the group consisting of Ag, Au, Cu, Pt, Al, Fe, Co, Ni, Ru, Rh, Pd, Ag doped with chlorine or chloride, and Au doped with chlorine or chloride.

25. The micro structure of claim 20, wherein the two or more structure layers comprise a material selected from the group consisting of $TiO_2$, $SiO_2$, $Al_2O_3$, $Si_3N_4$, $Ta_2O_5$, Zn oxide, Sn oxide, Sb oxide, Ag oxide, and Au oxide.

26. The micro structure of claim 20, wherein the two or more structure layers comprise a material selected from the group consisting of Ethylene Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), and Polyvinylprorolidone (PVP).

27. The micro structure of claim 20, wherein the two or more structure layers comprise a material selected from the group consisting of GaAs, ZnS, ZnO, CdS, $Er^3$ in $SiO_2$, InGaN, InGaN/GaN, AlGaAs, InAgAs, GaAs/GaAlAs, GaN, 4H SiC, AN, GaN, AlGaN/GaN, InP, InAlAs/InGaAs, Cs, Rb, diamond, InAs, AlSb/InAs, AlGaAs/InGaAs, InAlAs, InGaP, SiGe, Al, C and Si.

28. The micro structure of claim 20, wherein the adhesion layer comprises a metallic material.

29. The micro structure of claim 20, wherein the adhesion layer comprises a material selected from a group consisting of Ti, Ni, Co.

30. The micro structure of claim 20, wherein the thermal bias layer comprises a material selected from a group consisting of Cr, Pt, Ru, a Ni—Cr alloy, NiCrN, a Pt—Rh alloy, a Cu—Au—Co alloy, an Ir—Rh alloy, and a W—Re alloy.

31. The micro structure of claim 20, wherein one or more surfaces in the plurality of columns are configured to adsorb molecules of a trace chemical for detection of the trace chemical using Raman scattering.

32. The micro structure of claim 31, wherein the bias layer is configured to receive a bias voltage to enhance adsorption of molecules on the one or more surfaces in the plurality of columns for Raman scattering sensing of trace chemicals.

33. The micro structure of claim 31, wherein the molecules are adsorbed from a liquid, a gas, or a mixture of liquid and gas.

34. The micro structure of claim 20, wherein the plurality of columns distributed substantially in a periodic array in the two or more structure layers.

35. The micro structure of claim 20, wherein the center to center spacing between the adjacent columns in the plurality of columns is in the range of 0.5-1,000 nm.

36. The micro structure of claim 20, further comprising an upper layer on the two or more structure layers, wherein the upper layer comprises aluminum or PMMA.

37. The micro structure of claim 20, wherein a width of the plurality of columns are in the range of 5-200 nm.

38. The micro structure of claim 20, wherein the adhesion layer and the bias layer are formed by a single substantially uniform layer.

39. The micro structure of claim 20, wherein heights of the plurality of columns are in the range of 0.5 nm and 1000 nm.

40. A method for a micro structure, comprising:
   forming an adhesion layer on a substrate;
   forming a bias layer on the adhesion layer;
   two or more structure layers having different material compositions on the bias layer;
   forming an upper layer on the two or more structure layers, wherein the upper layer comprises a metallic material;
   forming a plurality of openings in the upper layer to produce a mask; and
   forming a plurality of columns having the two or more structure layers by removing portions of the two or more structure layers through the openings in the mask, wherein the widths of the plurality of columns are in the range of 0.5-500 nm.

41. The method of claim 40, wherein the upper layer comprises aluminum.

42. The method of claim 40, wherein the step of forming a plurality of columns comprises etching the two or more structure layers through the openings in the mask.

43. The method of claim 40, wherein the surfaces in the plurality of columns are configured to adsorb molecules of a trace chemical for detection of the trace chemical using Raman scattering.

44. The method of claim 43, wherein the adhesion layer is configured to receive a bias voltage to enhance adsorption of molecules on the one or more surfaces in the plurality of pores for Raman scattering sensing of trace chemicals.

45. The method of claim 44, wherein the bias layer is configured to be cooled to below room temperature to enhance adsorption of molecules on the one or more surfaces in the plurality of pores for Raman scattering sensing of trace chemicals.

* * * * *